United States Patent [19]

Cleary et al.

[11] Patent Number: 4,510,316

[45] Date of Patent: Apr. 9, 1985

[54] PURIFICATION OF N-METHYLPYRROLIDONE

[76] Inventors: James W. Cleary; Fred T. Sherk; Afif M. Nesheiwat, all c/o Phillips Petroleum Company, Bartlesville, Okla. 74004

[21] Appl. No.: 385,756

[22] Filed: Jun. 7, 1982

[51] Int. Cl.$^3$ .......................................... C07D 207/267
[52] U.S. Cl. .................................. 548/555; 528/388; 568/749; 260/705
[58] Field of Search ........................ 548/555; 568/749

[56] References Cited

U.S. PATENT DOCUMENTS 2,199,786  5/1940  Dierichs et al. .................... 568/749
3,658,659  4/1972  Cottle ................................ 548/555
3,697,487  10/1972  Cines ................................ 548/555
4,362,864  12/1982  Idel et al. ........................... 528/388

FOREIGN PATENT DOCUMENTS 48432  12/1974  Japan ................................ 548/555

Primary Examiner—Glennon H. Hollrah
Assistant Examiner—D. B. Springer

[57] ABSTRACT

Phenol is extracted with a chlorinated aromatic extractant, such as p-dichlorobenzene, from an aqueous mixture containing phenol and N-methylpyrrolidone. In an embodiment of this invention the purified N-methylpyrrolidone is recycled for use in a poly(phenylene sulfide) polymerization process.

16 Claims, 1 Drawing Figure

PURIFICATION OF N-METHYLPYRROLIDONE

This invention relates to a method for the extraction of phenol from an aqueous mixture containing phenol and N-methylpyrrolidone. This invention also relates to a method for the purification of N-methylpyrrolidone subsequent to its use in a poly(phenylene sulfide) polymerization process.

BACKGROUND

The preparation of poly(phenylene sulfide) can be accomplished by heating p-dichlorobenzene in the presence of a partially dehydrated mixture of sodium sulfide and N-methylpyrrolidone as disclosed in U.S. Pat. No. 3,354,129. U.S. Pat. No. 3,354,129 is incorporated by reference into this disclosure. After completion of the polymerization process, the poly(phenylene sulfide) can be recovered by flash evaporation of the volatile components, i.e., N-methylpyrrolidone, water, unreacted p-dichlorobenzene and volatile by-products of the polymerization reaction. U.S. Pat. Nos. 4,056,515 and 4,060,520 teach such a process and are incorporated by reference into this disclosure. A significant volatile by-product of the polymerization reaction is phenol. Other by-products include diphenyl ether and N-methyl-succinimide.

In order to recover N-methylpyrrolidone the flashed volatiles are fractionated in two successive distillation processes. The flashed volatiles are first passed to a "lights column" where water, unreacted p-dichlorobenzene and the more volatile by-products are removed overhead. The less volatile by-products (including phenol, diphenyl ether and N-methyl-succinimide) and N-methylpyrrolidone accumulate at the bottom of the "lights column." These kettle bottoms are subsequently fed into an "N-methylpyrrolidone recovery column" which generally operates at a temperature higher than that of the first column.

The overhead of the second recovery column is relatively pure N-methylpyrrolidone. Phenol, an impurity, accumulates at the bottom of the column so long as the phenol concentration in the kettle bottoms remains low (generally less than about 20 weight percent) and the temperature of the kettle bottoms remains low (generally below about 460° F.). Above these levels the phenol codistills with N-methylpyrrolidone. Because N-methylpyrrolidone is recycled to the polymerization step and because phenol adversely affects polymerization, codistillation of the phenol is highly undesirable.

It is well known that N-methylpyrrolidone (also called N-methyl-γ-butyrolactam) and phenol form a 1:1 adduct as disclosed in the Journal of Organic Chemistry 29, 3122–3124 (1964) incorporated by reference herein. This adduct formation apparently explains why phenol accumulates in the kettle bottoms even though it has a lower boiling point than N-methylpyrrolidone. Under the distillation conditions of the "N-methylpyrrolidone recovery column" a considerable excess of N-methylpyrrolidone relative to the amount of phenol present is necessary to preserve the thermal stability of the adduct. For this reason, a significant amount of N-methylpyrrolidone (about four times the amount of phenol) cannot be recovered by distillation since it must remain in the kettle bottom to bind phenol and thus prevent the phenol from distilling overhead and contaminating the N-methylpyrrolidone. This incomplete recovery is costly in that a valuable reagent is lost and kettle bottom disposal problems are magnified.

The kettle bottoms of the N-methylpyrrolidone recovery distillation column can be treated with neutral or acidic water to extract N-methylpyrrolidone. Although the water favors N-methylpyrrolidone over phenol (and the other impurities) a limited amount of phenol does enter the aqueous phase. The problem associated with the above-described water extraction of N-methylpyrrolidone in this concomitant transfer of some phenol to the aqueous phase. Removal of the transferred phenol is a necessary prerequisite to the recycling of N-methylpyrrolidone to the polymerization reactor because of the previously described interferring nature of phenol.

SUMMARY OF THE INVENTION

This invention is directed towards the purification of N-methylpyrrolidone in an aqueous phase containing phenol and N-methylpyrrolidone. The invention is practiced by contacting the aqueous phase with a chlorinated aromatic extractant such as p-dichlorobenzene. Upon contact with the aqueous phase the chlorinated aromatic will extract a disproportionately larger percentage of phenol than of N-methylpyrrolidone from the aqueous phase. This desired result is a consequence of the stronger affinity of the chlorinated aromatic for phenol than for N-methylpyrrolidone.

The chlorinated aromatic extractant can also be employed to facilitate phase separation of the aqueous and organic phases created by the water treatment of a mixture containing phenol and N-methylpyrrolidone such as, for example, water-treated kettle bottoms. Treatment of this mixture (e.g. kettle bottoms) with water (or acidic water) to extract N-methylpyrrolidone is useful only if the resultant aqueous and organic (or oil) phases can be separated. The physical nature of the phases created by water treatment of kettle bottoms is uncooperative towards this end. The density of the aqueous phase and the density of the organic (or oil) phase are only slightly different and therefore phase segregation requires relatively long undisturbed periods of time for the slightly heavier phase to settle below the slightly lighter phase. On a large commercial scale, the required settling period can be so time consuming as to make water extraction impracticable.

The density of the chlorinated aromatic extractants contemplated in the practice of this invention are generally significantly greater than the density of the aqueous phase. By treating the water-treated kettle bottoms with a chlorinated aromatic extractant, such as p-dichlorobenzene, the overall density of the organic phase is increased by virtue of the presence of the heavier extractant. The density differential between the aqueous and organic phases becomes sufficiently great such that the phases readily and rapidly separate. For the purposes of this aspect of this invention, those chlorinated aromatic extractants having a density greater than the density of the aqueous phase are useful. It is preferred that the density of the chlorinated aromatic extractant be at least about 1.10 g/cm$^3$. Specific examples of chlorinated aromatic extractants suitable for the promotion of phase separation are given in Example II. This aspect of the invention can be of advantage in both batch and continuous operations.

The scope of this invention is broader than its application to a poly(phenylene sulfide) polymerization process. Utility can be found in any application for which separation of phenol and N-methylpyrrolidone is desired. The invention broadly encompasses any extraction of phenol with a chlorinated aromatic extractant from an aqueous mixture containing phenol and N-methylpyrrolidone.

OBJECTS OF THE INVENTION

An object of this invention is to facilitate the recovery of N-methylpyrrolidone in a poly(phenylene sulfide) polymerization process.

Another object of this invention is to purify N-methylpyrrolidone by the disproportionate extraction of phenol from an aqueous mixture containing phenol and N-methylpyrrolidone.

These objects and other objects and advantages of the invention will be made apparent to a person of ordinary skill in the art from a study of this disclosure and the appended claims.

DETAILED DESCRIPTION OF THE INVENTION

Figure 1:
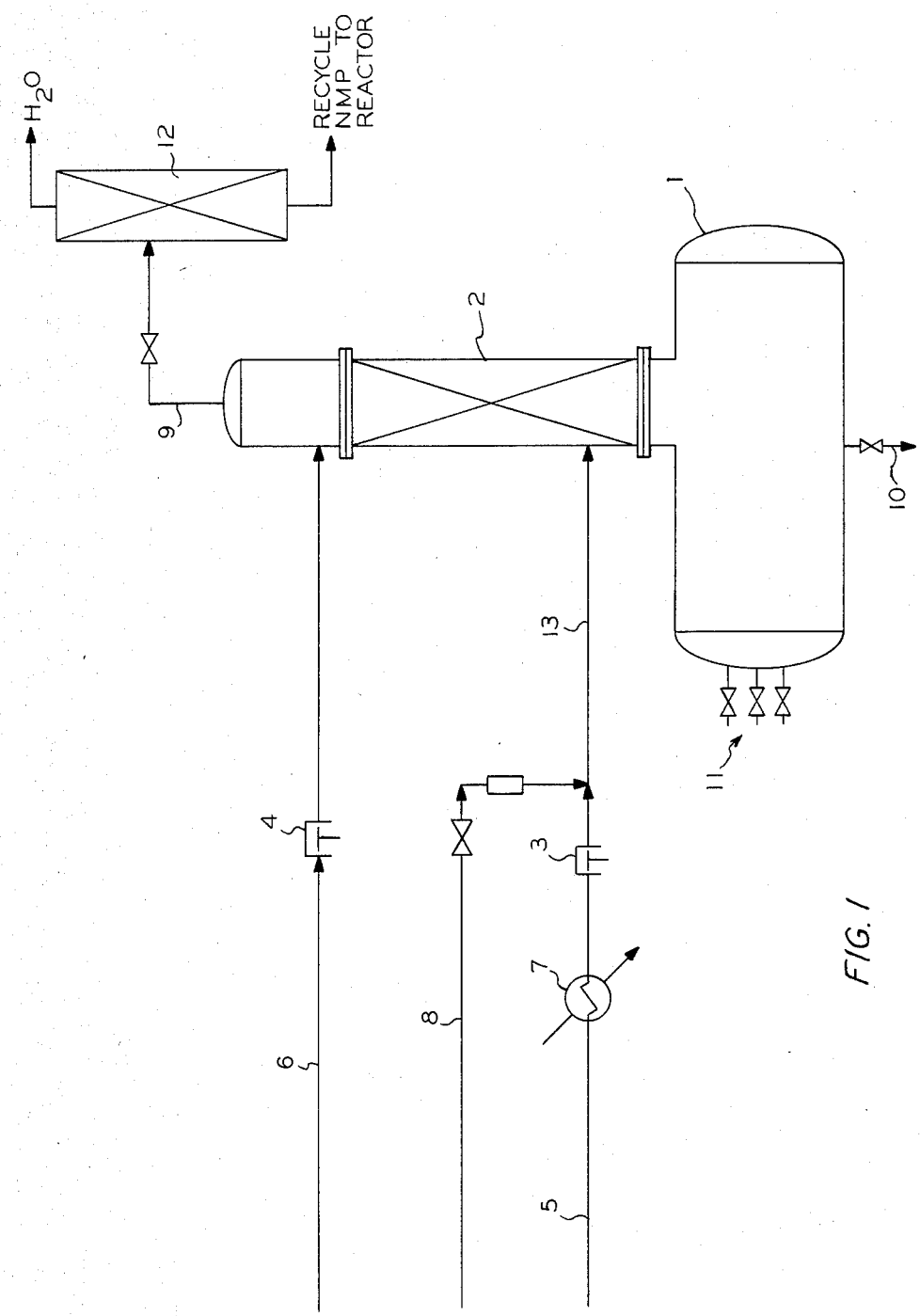
FIG. 1 is a drawing depicting a continuous process for the treatment of N-methylpyrrolidone-containing kettle bottoms.

Broadly, the scope of this invention encompasses a process for the purification of N-methylpyrrolidone by extracting phenol with a chlorinated aromatic extractant such as p-dichlorobenzene from an aqueous mixture containing phenol and N-methylpyrrolidone. The invention is particularly useful in a poly(phenylene sulfide) polymerization plant for purifying N-methylpyrrolidone recovered by extraction with neutral or acidic water from the kettle bottoms of an N-methylpyrrolidone recovery column.

When an aqueous mixture containing N-methylpyrrolidone and phenol is subjected to extraction with a chlorinated aromatic such as p-dichlorobenzene the weight percentage ratio of phenol to N-methylpyrrolidone will be higher in the resultant organic phase than in the resultant aqueous phase. In other words, the chlorinated aromatic extractant's stronger affinity for the phenol effectuates a disproportionate extraction in which a higher percentage of the phenol than of the N-methylpyrrolidone is extracted from the aqueous mixture.

This phenol-favoring nature of the chlorinated aromatic extractant provides the practitioner with an advantage sufficient to effect nearly complete removal of phenol from the N-methylpyrrolidone-containing aqueous mixture by repeating the extraction in several batch operations or by utilizing a continuous extraction process.

If the invention is used to facilitate recovery of N-methylpyrrolidone in a poly(phenylene sulfide) polymerization process it is preferable to pass the aqueous phase, after extraction with p-dichlorobenzene or some other chlorinated aromatic extractant, to a distillation column (e.g. the "lights column") to recover virtually phenol-free N-methylpyrrolidone recycle solvent.

The chlorinated aromatic compounds useful as extractants in the practice of this invention include, for example, chlorinated polycyclic aromatics such as chloronaphthalene and dichloronaphthalene. Also included are the chlorinated monocyclic aromatics such as, for example, benzyl chloride and methylbenzyl chloride. The preferred compounds are the chlorinated benzenes and their alkylated derivatives. Examples of the preferred compounds include, but are not limited to, chlorobenzene, chlorotoluene, chloroxylene, dichlorobenzene, dichlorotoluene, dichloroxylene, dichlorotrimethylbenzene and trichlorobenzene. It is intended that the above-identified compounds include all isomers (e.g. dichlorobenzene includes ortho-, meta- and para-dichlorobenzene). The presently most preferred compound, because of its availability and relatively high density, is para-dichlorobenzene referred to herein as p-dichlorobenzene.

If in addition to the chlorinated aromatic's utility as a phenol-favoring extractant, it is desired to use the chlorinated aromatic in the water-treated kettle bottoms of an N-methylpyrrolidone recovery distillation column, a chlorinated aromatic compound having a density greater than the density of the aqueous phase should be selected. For the purpose of phase separation, it is preferred that the chlorinated aromatic extractant have a density greater than about 1.10 g/cm$^3$. Those desiring to practice this invention can select a suitable chlorinated aromatic extractant by reference to chemical dictionaries and other publications which report the densities of such compounds. Methods for determining density are also well known in the art. Examples of some of the chlorinated aromatic extractants useful in promoting phase separation are identified in Example II.

The invention can be successfully practiced by using conventional liquid-liquid extraction techniques. Since extraction utilizes differences in the solubilities of the components it is desirable that the p-dichlorobenzene and the mixture containing phenol and N-methylpyrrolidone be brought into good contact to permit transfer of material. The extraction may be conducted batchwise or continuously. Suitable extraction equipment includes, for example, mixer-settlers, spray columns, packed columns, perforated-plate columns, baffle columns, and agitated towers. Given this disclosure, the extraction skills and knowledge possessed by those of ordinary skill in the art are sufficient to enable them to practice this invention.

The scope of our invention is not limited as to the amount of chlorinated aromatic extractant to be used. Good results are contemplated when the weight percentage ratio of chlorinated aromatic to phenol in the mixture containing phenol and N-methylpyrrolidone is from about 1:1 to about 20:1. The preferred range is from about 5:1 to about 15:1. Similarly, good results are contemplated when the weight percentage ratio of chlorinated aromatic to water in the mixture containing phenol and N-methylpyrrolidone is from about 1:1 to about 1:50. The preferred range is from about 1:2 to about 1:10.

Successful practice of the invention is contemplated at, but not limited to, extraction temperatures ranging from about 80° to about 250° F., (10°–121° C.) and extraction pressures ranging from about 0 to about 200 psig. Given this disclosure, optimum temperature, pressure and other operational parameters can be readily determined by a person of ordinary skill in the art. The essence of this invention resides in the use of a chlorinated aromatic extractant such as p-dichlorobenzene to effect a disproportionately phenol-favoring extraction of phenol from an aqueous mixture containing phenol and N-methylpyrrolidone.

The following examples illustrate the operability of our invention but should not be interpreted so as to unduly limit its scope.

EXAMPLE I

The data in this example show that p-dichlorobenzene (DCB) is a suitable extractant for removing a substantial amount of phenol from an aqueous mixture containing N-methylpyrrolidone (NMP) and phenol.

A mixture was prepared by combining together 299.5 grams of water, 20.0 grams of DCB, 20.0 grams of phenol and 102.1 grams of NMP. The system was vigorously mixed above the crystallization temperature of the organic phase (about 140° F.). The aqueous phase and the organic (oil) phase were allowed to form and were then separated in a separatory funnel and analyzed by a Perkin Elmer Sigma 3 gas chromatograph filled with 6% K20M (Carbowax poly(ethylene glycol)) on 35/60 mesh Chromasorb T.

Evaluation of the peak areas of the gas chromatogram revealed the following amounts and percentages (based on the original system before agitation) summarized in Table I.

TABLE I

|  | Organic Phase | Aqueous Phase |
| --- | --- | --- |
| Phenol, grams | 8.21 | 11.8 |
| Phenol, % (based on total phenol) | 41.0 | 59.0 |
| NMP, grams | 7.46 | 94.7 |
| NMP, % (based on total NMP) | 7.3 | 92.7 |
| DCB, grams | 17.57 | 2.43 |
| DCB, % (based on total DCB) | 87.8 | 12.2 |
| Water, grams | 3.21 | 296.3 |
| Water, % (based on total water) | 1.1 | 98.9 |

The data in Table I show that 41% of the phenol accumulated in the organic phase, whereas only about 7% of the NMP accumulated in the organic phase. This evidences the stronger affinity of the DCB extractant for phenol than for NMP. Further extraction of the aqueous phase with DCB, either in several batch extraction stages or in a continuous, preferably counter-current extraction process, would result in the essentially quantitative removal of phenol from the aqueous phase. The major portion of NMP remains in the aqueous phase.

EXAMPLE II

This example illustrates an embodiment of this invention and its presently-contemplated best mode of operation by describing a continuous process for the purification of N-methylpyrrolidone (NMP) in a polyphenylene sulfide) polymerization process. This continuous process is an integration of the steps necessary to recover NMP from the kettle bottoms of an "NMP recovery column" in a form sufficiently pure to permit recycle of the NMP to the polymerization reactor.

Attention is courteously directed to FIG. 1 where the apparatus of the process is depicted. A cylindrical steel tank 1 is positioned beneath, and in open communication with, a liquid-liquid steel extraction column 2. The tank 1 is about 2 feet in diameter and about 6 feet in length. The extraction column 2 is about 3 inches in diameter and about 12 feet high. The valves 11 at the side of the tank 1 are for taking samples from the tank. The extraction column 2 is filled with ⅝″ pallring packing.

A stainless steel Milton Roy diaphragm pump 3 pumps a stream 5 of material from the kettle bottoms of a "NMP recovery column" (also called a "heavies column") in a poly(phenylene sulfide) polymerization plant. The components of stream 5 include NMP and phenol. The pump operates at a rate of 6.5 gph (gallons per hour). The kettle bottoms in stream 5 are removed from the "NMP recovery column at a temperature of about 430° F. Stream 5 is cooled to about 175° F. by a heat exchanger 7 and then fed to the lower portion of the extraction column 2.

A second stainless steel Milton Roy diaphragm pump 4 pumps a stream 6 of DCB extractant to the extraction column 2 at a rate of about 2 to about 4 gph (gallons per hour). The temperature of the DCB passing into the upper portion of the extraction column 2 is about 180° F.

Water in stream 8 is introduced into the kettle bottom stream 5 at a rate of about 8 to about 10 gph to form stream 13. This pretreatment of the kettle bottoms with water creates an aqueous phase and an organic (or oil) phase. As desired, the water extracts NMP from the kettle bottoms. Although the water favors NMP over phenol in this extraction some phenol is transferred to the aqueous phase. Further separation of NMP from phenol is accomplished in the extraction column 2.

As stream 13 enters the extraction column 2 the aqueous and organic (or oil) phases in stream 13 are substantially intermixed. Because the difference in density between the two phases is slight it is difficult, especially in large scale commercial operations, to separate the phases. Normally, a long period of time would be required to allow the phases to settle and segregate before separation would become feasible. One significant advantage of this invention as described in this example is the use of a chlorinated aromatic extractant such as DCB to not only extract phenol but to also facilitate separation of the aqueous and organic phases. This phase-separation-promoting utility is a consequence of the relatively higher density of DCB as compared to either the aqueous or organic phase in stream 13. Upon entering the extraction column 2 the stream 13 comes into contact with the downwardly flowing DCB. The DCB becomes, in effect, part of the organic phase. The density of the organic phase is significantly increased by the presence of the DCB and as a consequence of the density differential the phases readily separate.

The bulk of the heavier, DCB-containing organic phase passes to the tank 1. The aqueous phase progresses upwardly through the extraction column 2 in countercurrent contact with the DCB extractant. Because of the phenol-favoring nature of the DCB extractant (as evidenced by the single batch experiment of Example I) the continuous countercurrent extraction in column 2 results in a nearly quantitative removal of phenol from the NMP-containing aqueous phase.

The overhead 9 primarily comprises water and NMP. Only very small amounts of phenol and DCB are present. The overhead can be passed to a distillation column 12 (e.g. the "lights column") to remove water and to recover NMP for recycle to the poly(phenylene sulfide) polymerization reactor.

The bulk of the DCB extractant and of the phenol (and other kettle bottom raffinate) are drained from the tank 1 by drain means 10.

The integrated continuous process illustrated in this example is not limited to the specific apparatus and process parameters recited above. The heart of this integrated continuous process lies in mixing water (or acidic water) with the kettle bottoms of an "NMP recovery column" to form a first stream which is passed to an extraction column and in passing a second stream of a chlorinated aromatic extractant to the same column at some point in the column above the point at which the first stream is introduced.

Although all chlorinated aromatic extractants are contemplated to be useful it is noted that the densities of some (e.g. 3-chlorotoluene, 2-chloro-1,4-dimethylbenzene and (1-chloroethyl)benzene) are relatively low, i.e. below about 1.10 g/cm$^3$, and therefore may not enhance separation of the aqueous and organic phases in the extraction column as well as the heavier extractants. Although this aspect of the invention (i.e. the integrated continuous process) is not limited thereto, chlorinated aromatic extractants sufficiently heavy (i.e. density greater than about 1.10 g/cm$^3$) to give good results along the lines of enhanced phase separation include, for example:

p-dichlorobenzene, m-dichlorobenzene,
o-dichlorobenzene, 1,2,4-trichlorobenzene,
1,2-dichloronaphthalene,
1,4-dichloronaphthalene, and all of the dichlorotoluenes.

Generally in this integrated continuous process it is contemplated that good results can be achieved by operating within the following ranges:

(1) Weight ratio of chlorinated aromatic extractant to "NMP recovery column" kettle bottoms: from about 1:20 to about 2:1, preferably from about 1:5 to about 1:1.

(2) Weight ratio of chlorinated aromatic extractant to water: from about 1:1 to about 1:50, preferably from about 1:2 to about 1:10.

(3) Temperature in tank and extraction column: from about 150° F. to about 300° F., preferably from about 160° F. to about 200° F.

(4) Pressure in the tank and extraction column should be sufficient to keep all components in the liquid state: from about 5 to about 200 psig, preferably from about 15 to about 35 psig.

EXAMPLE III

Three representative liquid-liquid extraction runs employing the unit specifically described in Example II were carried out with the "NMP recovery column" kettle bottoms of a Ryton ® poly(phenylene sulfide) polymerization plant. Data corresponding to the feed, overhead and bottom effluents were obtained by gas chromatography analysis. In each run overhead effluent samples were taken and analyzed at intervals of about 1 to 2 hours. In each run one tank bottom effluent sample was taken and analyzed about 1 to 3 hours before the end of the run. Each run lasted about 10 hours. Feed rates and analysis data for each of the three representative runs A, B and C are presented in Table II below.

TABLE II

| | Run A | Run B | Run C |
| --- | --- | --- | --- |
| Kettle Bottoms (5) Feed Rate (gallons per hour) | 6.5 | 6.5 | 6.5 |
| Water (8) Feed Rate (gallons per hour) | 8–10[a] | 8–10[a] | 8–10[a] |
| DCB (6) Feed Rate (gallons per hour) | 2–4[a] | 2–4[a] | 2–4[a] |
| Phenol in Kettle Bottom Feed (5) (weight %) | 5.2 | 5.9 | 6.0 |
| NMP in Kettle Bottom Feed (5) (weight %) | 55–65[b] | 55–65[b] | 55–65[b] |
| H$_2$O in Overhead Effluent (9) (weight %) | 86.3[c] | 85.1[d] | 83.9[e] |
| NMP in Overhead Effluent (9) (weight %) | 12.9[c] | 14.4[d] | 15.6[e] |
| DCB in Overhead Effluent (9) (weight %) | 0.14[c] | 0.07[d] | 0.12[e] |
| Phenol in Overhead Effluent (9) (weight %) | 0.22[c] | 0.18[d] | 0.24[e] |
| H$_2$O in Tank Bottom Effluent (10) (weight %) | ~0 | ~0 | ~0 |
| NMP in Tank Bottom Effluent (10) (weight %) | 11.0 | 12.0 | 11.9 |
| DCB in Tank Bottom Effluent (10) (weight %) | 69.0 | 68.0 | 73.0 |
| Phenol in Tank Bottom Effluent (10) (weight %) | 7.5 | 8.0 | 7.8 |

[a]Crude DCB containing some water was used causing the actual DCB and H$_2$O feed rates to vary as indicated.
[b]Plant analyses of the kettle bottoms at the approximate time of the test runs yielded weight percentages generally falling within this range.
[c]Average of 9 samples.
[d]Average of 6 samples.
[e]Average of 6 samples. Two samples with excessively high phenol weight percentages were disregarded because they were taken at times (1 and 2 hours after start-up) when steady state conditions had not yet been attained (mainly because of clogging problems in the DCB feed line).

Data in Table II show that the overhead effluent 9 contained only small amounts of phenol (i.e. 0.18–0.24 weight percent). The data indicate further that the weight percentage ratio of NMP to phenol in the overhead effluent 9 ranged from about 60 to 1 (Run A) to about 80 to 1 (Run B). This represents a considerable improvement over the 10 to 1 NMP to phenol weight percentage ratio found in the kettle bottom feed 5. The NMP to phenol weight percentage ratio in the tank bottom effluent 10 was about 1.5 to 1.

A reasonable estimate of the NMP recovery efficiency of this continuous process was calculated to be about 80 percent (i.e. about 80 percent of the NMP in the kettle bottoms was recovered). The recovered NMP was available for recycle to the polymerization reactor.

The NMP recovery efficiency calculation was based upon the following estimates:

(a) during each 10 hour run 50 gallons of tank bottom effluent were collected;

(b) the kettle bottom feed density was 1.05 g/cc (estimated from NMP and phenol densities);

(c) the NMP content of the kettle bottom feed was 60 weight percent;

(d) the average density of the unidentified impurities in the kettle bottom feed and in the tank bottom effluent was equal to the density of phenol, i.e. 1.07 g/cc;

(e) the weight percentage of DCB in the tank bottom effluent was 70 percent;

(f) the weight percentage of NMP in the tank bottom effluent was 12 percent;

(g) the weight percentage of phenol plus other impurities in the tank bottom effluent was 18 percent.

These reasonable estimates and the data in Table II were used as follows to calculate the efficiency of the process:

During each 10 hour run, 65 gallons (6.5 gal/hr × 10 hr) of kettle bottom feed weighing 570 lb (1.05 g/cc × 8.345 (lb/gal)/(g/cc × 65 gal) were charged to the extraction column. The kettle bottom feed contained 342 lb (570 lb × 0.60) of NMP.

The tank bottom effluent density was calculated from the densities and weight percentages of DCB, NMP and phenol (plus the unidentified impurities) as set forth below:

$$\left(1.48 \frac{\text{g DCB}}{\text{cc}} \times .70\right) + \left(1.03 \frac{\text{g NMP}}{\text{cc}} \times .12\right) +$$

$$\left(1.07 \frac{\text{g phenol + impurities}}{\text{cc}} \times .18\right) = 1.35 \text{ g/cc}$$

Thus 50 gallons of tank bottom effluent collected during a 10 hour run weighed about 563 lb (1.35 g/cc×8.345 (lb/gal)/g/cc)×50 gal) and contained about 67.6 lb (563 lb×0.12) of NMP. This represents about 20 weight percent of the 342 lb of NMP that entered the extraction column as part of the kettle bottom feed. The remaining 80 percent of the NMP accumulated in the overhead effluent and was available for recycle.

The examples have been given to illustrate this invention and should not be interpreted to unduly limit its scope. This invention broadly encompasses the extraction with a chlorinated aromatic extractant of phenol from an aqueous mixture containing phenol and N-methylpyrrolidone. The integrated continuous process described in Examples II and III is the presently preferred application of this invention.

Reasonable variations from and modifications of my invention as herein disclosed, not departing from the essence thereof, are contemplated to be within the scope of patent protection desired and sought.

We claim:

1. A method for purification of N-methylpyrrolidone from a mixture comprising N-methylpyrrolidone, phenol and water, said method comprising:

extracting phenol with a chlorinated aromatic extractant from said mixture; wherein said chlorinated aromatic extractant has a density of at least about 1.10 g/cm$^3$.

2. A method in accordance with claim 1 wherein said mixture is contacted with said chlorinated aromatic extractant to form an aqueous phase and an organic phase; and wherein the weight percentage ratio of phenol to N-methylpyrrolidone in said organic phase is greater than the weight percentage ratio of phenol to N-methylpyrrolidone in said aqueous phase.

3. A method according to claim 1 wherein said extractant is a chlorinated monocyclic aromatic.

4. A method according to claim 3 wherein said extractant is a member of the group consisting of chlorinated benzenes and their alkylated derivatives.

5. A method according to claim 4 wherein said extractant is a member of the group consisting of chlorobenzene, chlorotoluene, chloroxylene, dichlorotoluene, dichloroxylene, dichlorotrimethylbenzene and trichlorobenzene.

6. A method according to claim 2 or 4 wherein said extractant is dichlorobenzene.

7. A method according to claim 6 wherein said extractant is para-dichlorobenzene.

8. A method comprising:
    (a) contacting a mixture comprising phenol and N-methylpyrrolidone with water;
    (b) extracting phenol from the water-contacted mixture produced in (a) in accordance with the method of claim 1 or 7.

9. A method comprising:
    (a) extracting N-methylpyrrolidone with water from the kettle bottoms of an N-methylpyrrolidone recovery distillation column; wherein said extraction with water produces an aqueous phase comprising N-methylpyrrolidone, phenol and water; and
    (b) extracting phenol from said aqueous phase in accordance with the method of claim 1.

10. A continuous process in accordance with claim 9 wherein said kettle bottoms and said water are combined and introduced in a continuous manner into an extraction column; wherein said chlorinated aromatic extractant is introduced in a continuous manner into said extraction column; and wherein continuous countercurrent extraction of said phenol from said aqueous phase occurs in said extraction column.

11. A continuous process in accordance with claim 10 wherein the weight ratio of said chlorinated aromatic extractant to said kettle bottoms is within the range of about 1:5 to about 1:1; and wherein the weight ratio of said chlorinated aromatic extractant to said water is within the range of about 1:2 to about 1:10.

12. A method in accordance with claim 10 or 11 wherein said chlorinated aromatic extractant is para-dichlorobenzene.

13. A method in accordance with claim 10 or 11 wherein the density of said chlorinated aromatic extractant is sufficiently high to cause rapid phase separation in said extraction column.

14. A method in accordance with claim 1, 7, 8, 10 or 11 wherein said N-methylpyrrolidone is recycled to a poly(phenylene sulfide) reaction zone after extraction of said phenol from said aqueous mixture.

15. A method according to claim 1 comprising:
    extracting phenol with a chlorinated aromatic extractant from an aqueous mixture;
    wherein said aqueous mixture comprises N-methylpyrrolidone, phenol and water and wherein said chlorinated aromatic extractant is selected from the group consisting of chlorinated benzenes and their alkylated derivatives.

16. A method according to claim 15 wherein said extractant is para-dichlorobenzene.

* * * * *